(12) United States Patent
Rettedal et al.

(10) Patent No.: US 10,231,644 B2
(45) Date of Patent: Mar. 19, 2019

(54) CALF BOLUS

(71) Applicant: ST Reproductive Technologies, LLC, Navasota, TX (US)

(72) Inventors: Nicholas P. Rettedal, Loveland, CO (US); Stephen M. Weilnau, Greeley, CO (US); Scott R. Cockroft, Greeley, CO (US); Joseph Janus, IV, Loveland, CO (US)

(73) Assignee: ST Reproductive Technologies LLC, Navasota, TX (US)

( * ) Notice: Subject to any disclaimer, the term of this patent is extended or adjusted under 35 U.S.C. 154(b) by 0 days.

(21) Appl. No.: 14/738,789

(22) Filed: Jun. 12, 2015

(65) Prior Publication Data

US 2016/0360994 A1 Dec. 15, 2016

(51) Int. Cl.
| | |
|---|---|
| *A61B 5/07* | (2006.01) |
| *A61B 5/0205* | (2006.01) |
| *A61B 5/00* | (2006.01) |
| *A01K 11/00* | (2006.01) |
| *A61B 5/01* | (2006.01) |
| *A61B 5/024* | (2006.01) |
| *A61B 5/11* | (2006.01) |

(52) U.S. Cl.
CPC .......... *A61B 5/073* (2013.01); *A01K 11/007* (2013.01); *A61B 5/0031* (2013.01); *A61B 5/02055* (2013.01); *A61B 5/4238* (2013.01); *A61B 5/6861* (2013.01); *A61B 5/01* (2013.01); *A61B 5/024* (2013.01); *A61B 5/11* (2013.01); *A61B 2503/40* (2013.01); *A61B 2560/0209* (2013.01)

(58) Field of Classification Search
CPC ....... A61B 5/073; A61B 5/076; A61B 5/0031; A61D 7/00; A01K 11/006–11/008
See application file for complete search history.

(56) References Cited

U.S. PATENT DOCUMENTS

| | | | |
|---|---|---|---|
| 5,482,008 A | 1/1996 | Stafford et al. | |
| 5,532,692 A | 7/1996 | Tatsuya | |

(Continued)

FOREIGN PATENT DOCUMENTS

| | | |
|---|---|---|
| EP | 2314154 A1 | 4/2011 |
| JP | 2007089892 | 4/2007 |

(Continued)

OTHER PUBLICATIONS

European Patent Application No. 11834759.0; Office Action dated May 24, 2016, 8 pages total.

(Continued)

*Primary Examiner* — Tammie K Marlen
(74) *Attorney, Agent, or Firm* — Ryan Christensen; Hashim Rahman

(57) ABSTRACT

An animal monitoring device configured as a bolus for oral administration to reside in the reticulorumen of a ruminant animal. The animal monitoring device includes a memory element, a processor in communication with the memory element and a computer code contained in the memory element. The computer code includes a power management module executable by the processor to regulate power use by the bolus based on determination of remaining energy stored in an energy source and the determined power requirements over a pre-determined life cycle of the bolus.

19 Claims, 7 Drawing Sheets

(56) References Cited

U.S. PATENT DOCUMENTS

| | | | |
|---|---|---|---|
| 5,818,354 A | 10/1998 | Gentry | |
| 5,963,132 A | 10/1999 | Yoakum | |
| 5,984,875 A | 11/1999 | Brune | |
| 6,059,733 A | 5/2000 | Brune et al. | |
| 6,085,751 A | 7/2000 | Taparia | |
| 6,099,482 A | 8/2000 | Brune et al. | |
| 6,371,927 B1 * | 4/2002 | Brune | A61B 18/14 600/549 |
| 6,416,782 B1 | 7/2002 | Maas | |
| 6,702,185 B1 | 3/2004 | Zercher | |
| 7,441,515 B2 | 10/2008 | Renz et al. | |
| 7,962,096 B2 | 6/2011 | Cox | |
| 8,001,168 B2 | 8/2011 | Tsuyuzaki | |
| 8,545,436 B2 | 10/2013 | Robertson et al. | |
| 8,547,248 B2 | 10/2013 | Zdeblich et al. | |
| 8,588,887 B2 * | 11/2013 | Arneson | A61B 5/0002 600/407 |
| 8,640,712 B2 | 2/2014 | Ardrey, Jr. | |
| 8,694,091 B2 | 4/2014 | Birk et al. | |
| 8,771,201 B2 | 7/2014 | Gabriel et al. | |
| 8,823,515 B2 | 9/2014 | Rettedal et al. | |
| 2001/0001176 A1 | 5/2001 | Caja Lopez et al. | |
| 2002/0128542 A1 | 9/2002 | Van Over | |
| 2004/0133131 A1 | 7/2004 | Kuhn et al. | |
| 2004/0155782 A1 | 8/2004 | Letkomiller et al. | |
| 2005/0134452 A1 | 6/2005 | Smith | |
| 2005/0145187 A1 | 7/2005 | Gray | |
| 2007/0136154 A1 | 6/2007 | Chung | |
| 2007/0156016 A1 | 7/2007 | Betesh et al. | |
| 2008/0104209 A1 | 5/2008 | Singhal et al. | |
| 2008/0236500 A1 | 10/2008 | Hodges et al. | |
| 2008/0314325 A1 | 12/2008 | Hempstead et al. | |
| 2009/0030279 A1 * | 1/2009 | Zander | A61B 1/00036 600/118 |
| 2009/0182207 A1 | 7/2009 | Riskey et al. | |
| 2009/0187392 A1 | 7/2009 | Riskey et al. | |
| 2010/0030025 A1 | 2/2010 | Segawa et al. | |
| 2010/0302039 A1 | 12/2010 | Goto et al. | |
| 2011/0212782 A1 | 9/2011 | Thompson et al. | |
| 2011/0301437 A1 | 12/2011 | Gabriel et al. | |
| 2012/0068848 A1 | 3/2012 | Campbell et al. | |
| 2013/0197323 A1 | 8/2013 | Rettedal et al. | |
| 2013/0231188 A1 | 9/2013 | Berberich et al. | |
| 2014/0240088 A1 | 8/2014 | Robinette et al. | |
| 2014/0368338 A1 | 12/2014 | Rettedal et al. | |

FOREIGN PATENT DOCUMENTS

| | | |
|---|---|---|
| WO | WO 2011/079338 A2 | 7/2011 |
| WO | WO 2012/173502 A1 | 12/2012 |
| WO | 2016/201242 | 12/2016 |

OTHER PUBLICATIONS

Boehmer, et al. Effects of Temperature of Consumed Water on Rumen Temperature of Beef Cows. Oklahoma Agricultural Experiment Station, 2009, 4 total pages.

Caja et al. Development of a ceramic bolus for the permanent electronic identification of sheep, goat and cattle. Computers and Electronics in Agriculture (1999), vol. 24, pp.

Cooper-Prado, et al. Relationship of Ruminal Temperature with Parturition and Estrus of Beef Cows. J Anim Sci, Apr. 2011, 89:1020-1027; published ahead of print Dec. 17, 2011.

Fallon et al. Electronic Animal Identification. Grange Research Center, Beef Production Series No. 46, pp. 1-54.

Ghirardi et al. Evaluation of the retention of electronic identification boluses in the forestomachs of cattle. Journal of Animal Science (2006), vol. 84, pp. 2260-2268.

Ghirardi et al. Retention of different sizes of electronic identification boluses in the forestomachs of sheep. Journal of Animal Science (2006), vol. 84, pp. 2865-2872.

Hach. Digital Inductive Conductivity Sensor, Convertible Body Style. Website, http:/www.hach.com, product page downloaded Mar. 5, 2014, 2 total pages.

Scanga et al. Development of computational models for the purpose of conducting individual livestock and premises traceback investigations utilizing.

Smartstock USA. Website, http://www.smartstock-usa.com, originally downloaded Dec. 30, 2011, 12 total pages.

Corresponding AU Patent Application No. 2010296053; Patent Examination Report No. 1, dated Jul. 16, 2014, 3 total pages.

Corresponding New Zealand patent application No. 599357; Letters Patent dated Sep. 3, 2012, 1 page.

Corresponding New Zealand patent application No. 599357; OA dated Oct. 19, 2012, 1 page.

Corresponding New Zealand patent application No. 599357; OA dated Feb. 8, 2013, 1 page.

Corresponding New Zealand Patent Application No. 610343; OA mailed May 12, 2013, 3 total pages.

New Zealand patent application No. 610343; OA dated Nov. 11, 2013, 3 total pages.

Carné et al. Modeling the retention of rumen boluses for the electronic identification of goats. J Dairy Sci, Feb. 2011, 94(2), pp. 716-726 (abstract only, 2 pages total).

Ghirardi et al. Retention of different sizes of electronic identification boluses in the forestomachs of sheep. J Anim Sci, Nov. 2006, 84(10), pp. 2865-2872.

International PCT Patent Application No. PCT/US2016/066012; International Search Report and Written Opinion dated Mar. 3, 2017, 9 pages total.

\* cited by examiner

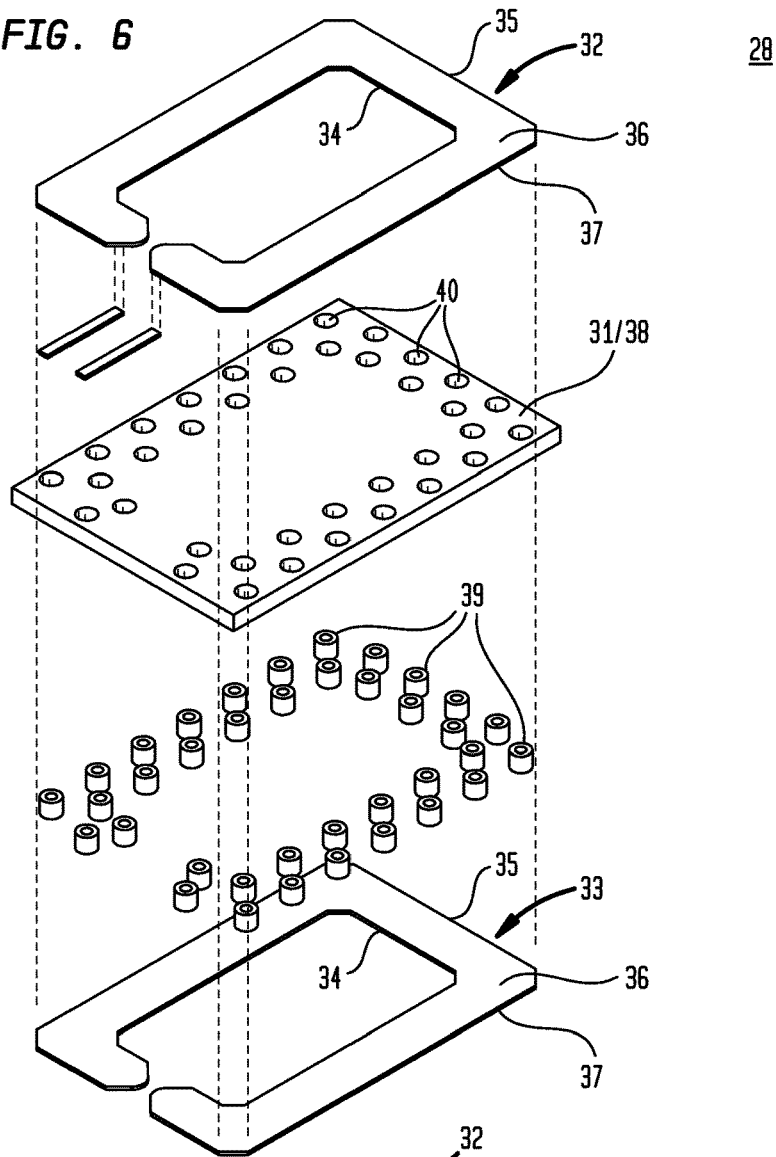
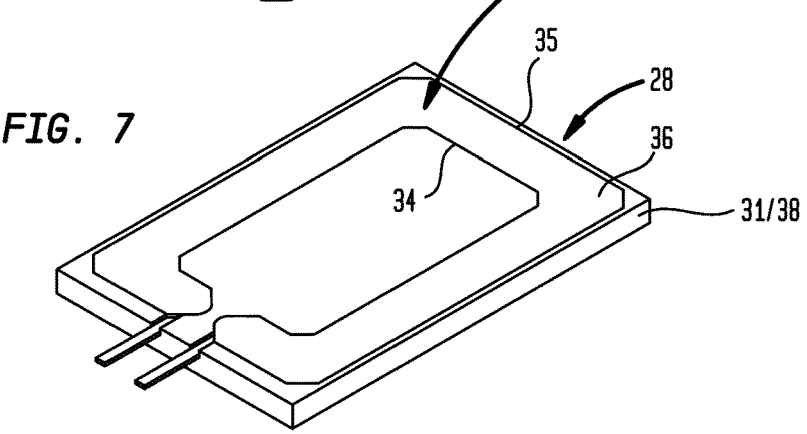

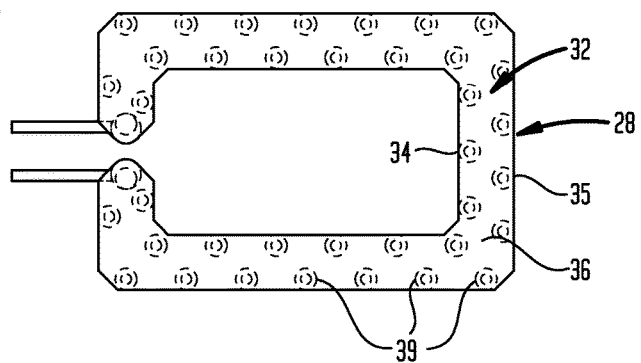
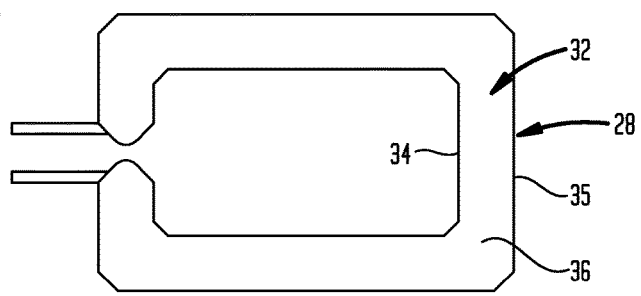
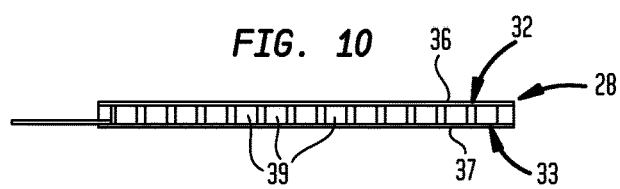
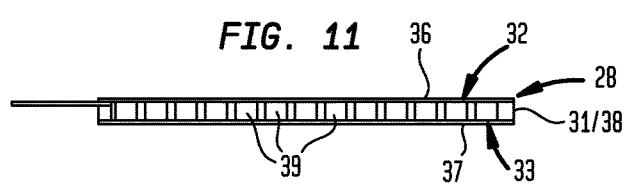
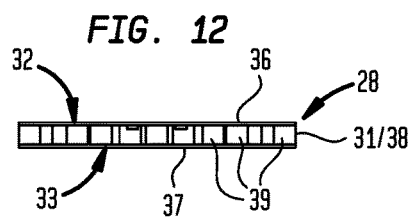
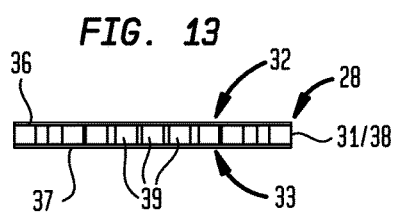

CALF BOLUS

I. FIELD OF THE INVENTION

An animal monitoring device configured as a bolus for oral administration to reside in the reticulorumen of a ruminant animal. The animal monitoring device includes a memory element, a processor in communication with the memory element and a computer code contained in the memory element. The computer code includes a power management module executable by the processor to regulate power use by the bolus based on determination of remaining energy stored in an energy source and the determined power requirements over a pre-determined life cycle of the bolus.

II. BACKGROUND OF THE INVENTION

Conventional boluses orally administered to reside in the reticulorumen for monitoring of physiological parameters of ruminant animals may not have a configuration capable of oral administration at birth. Additionally, boluses even when orally administered to adult ruminant animals may not have an operational lifespan long enough to monitor useful physiological parameters over the remaining productive lifespan of the ruminant animal. Moreover, uncontrollable changes in the orientation of the bolus and correspondingly uncontrolled orientation of the bolus antenna in the reticulorumen of the ruminant animal may cause variable quality in radio signal transmission from the ruminant animal resulting in the loss of encoded physiological data.

III. SUMMARY OF THE INVENTION

Accordingly, a broad object of the invention can be to provide a bolus having an outer most surface configuration and a density which allows oral administration to a ruminant animal immediately after birth and prevents or substantially reduces the likelihood of being regurgitated or ejected from the reticulorumen of a ruminant animal over the entire lifespan or productive lifespan of the ruminant animal.

Another broad object of the invention can be to provide a bolus which can reside in the reticulorumen of a ruminant animal having an operational lifespan corresponding to the entire lifespan or the productive lifespan of the ruminant animal. One aspect of this broad object of the invention involves a power management module including an activation element which maintains the bolus in a sleep mode in which one or more encoded sensor signals are compared to a pre-selected activation code and upon achieving a pre-selected activation match threshold between the encoded sensor signals and the pre-selected activation code causes the bolus to be activated for normal monitoring of one or more physiological parameters of the ruminant animal. As to particular embodiments, a first and second pre-selected activation match threshold can be met by comparison of a corresponding first and second encoded sensor signals and a first and second pre-selected activation code to provide assurance that environmental events to not inadvertently activate the bolus for normal monitoring. Another aspect of this broad object of the invention involves a power management module pre-programmed or re-programmable to reconfigure the operating parameters of the bolus during residence in the reticulorumen of a ruminant animal to collect only useful physiological data and encode and transmit such physiological data at intervals based upon the life stage of the ruminant animal. Another aspect of this broad object of the invention involves a power management module which functions to evaluate the remaining amount of energy stored in the power source of the bolus and compare the remaining amount of energy to the energy requirements of the bolus during a pre-determined period of time based on the existing programmed operational parameters of the bolus and further functions to employ power regulation events to offset the difference between the energy requirement of the bolus over the pre-determined period of time and the amount of energy remaining in the power source.

Another broad object of the invention can be to provide an antenna having a structure that alters the magnetic field and electrical field generation in a manner that reduces the impact of uncontrollable changes in the orientation of the bolus and correspondingly the orientation of the antenna during residence of the bolus in the reticulorumen of the ruminant animal.

Naturally, further objects of the invention are disclosed throughout other areas of the specification, drawings, photographs, and claims.

IV. BRIEF DESCRIPTION OF THE DRAWINGS

FIG. 6 is an exploded view of a particular embodiment of an antenna included in the particular embodiment of the bolus shown in FIGS. 4 and 5.

FIG. 7 is a top perspective view of the particular embodiment of the antenna shown in FIG. 6 having first and second electrically conductive loops disposed on the opposed surfaces of a non-electrically conductive sheet material.

FIG. 8 is top plan view of the particular embodiment of the antenna shown in FIG. 6 with vias (shown in broken line) interconnecting a first and second electrically conductive loops without being disposed on opposed surfaces of a non-electrically conductive sheet material.

FIG. 9 is a top plan view of the particular embodiment of the antenna shown in FIG. 8.

FIG. 10 is a first side elevation view of the particular embodiment of the antenna shown in FIG. 8.

FIG. 11 is a second side elevation view of the particular embodiment of the antenna shown in FIG. 8.

FIG. 12 is a first end elevation view of the particular embodiment of the antenna shown in FIG. 8.

FIG. 13 is a second end elevation view of the particular embodiment of the antenna shown in FIG. 8.

V. DETAILED DESCRIPTION OF THE INVENTION

Figure 1:
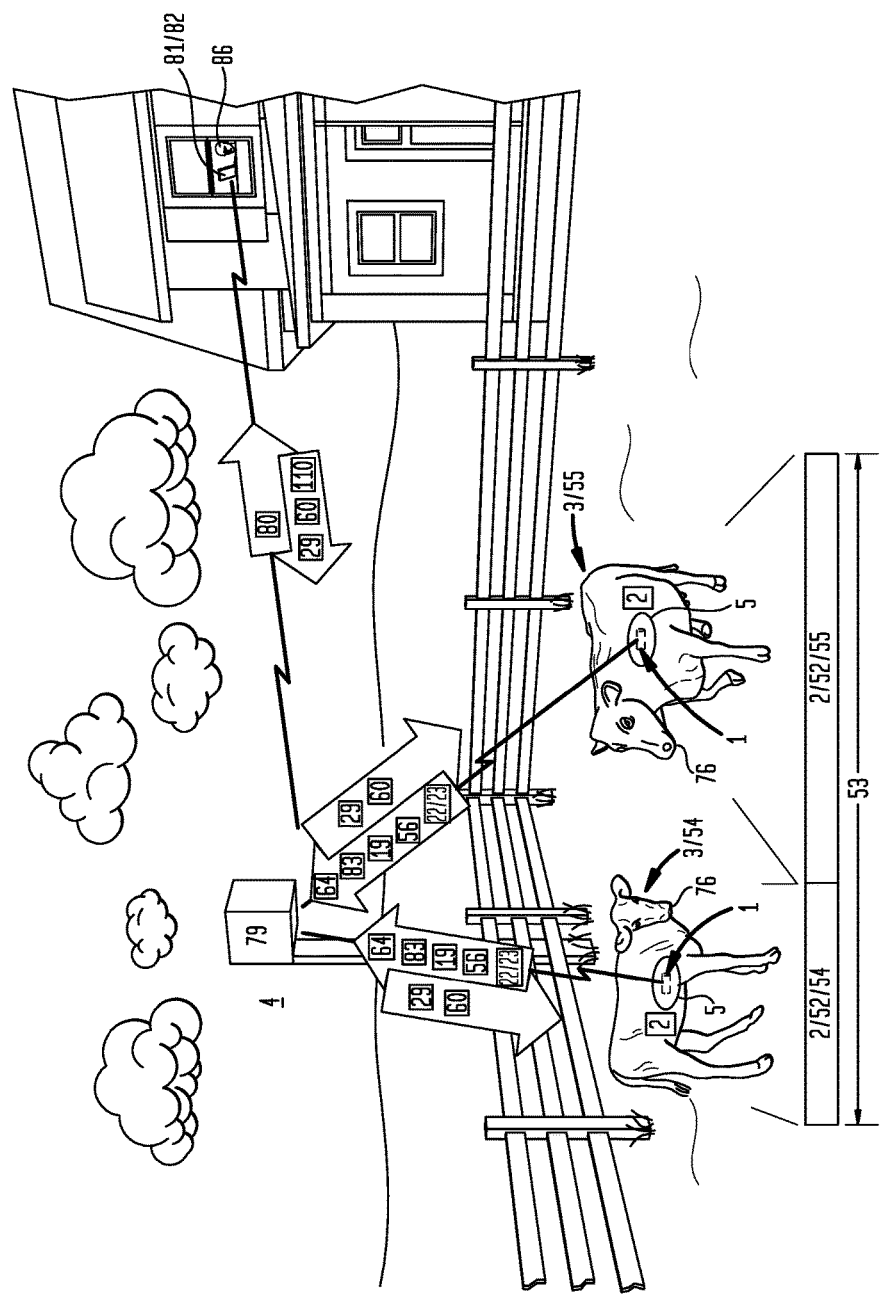
FIG. 1 is a diagram which shows a particular method of using an embodiment of the animal monitoring system to monitor one or more physiological parameters of a ruminant animal.

Now generally referring to FIGS. 1 through 13, which provide illustrative examples of an inventive bolus (1) and a method of using a bolus (1) to monitor one or more physiological parameters (2) of a ruminant animal (3) and a computer implemented animal monitoring system (4). The bolus (1) can be orally administered to reside in the reticulorumen (5) of the ruminant animal (3). As to certain embodiments, the bolus (1) can include a bolus body (6) having an outer most external surface (7) configured to allow oral administration to a ruminant animal (3), with certain embodiments capable of being orally administered immediately after birth. As to certain embodiments, the bolus (1) can include a microcontroller (8) including a processor (9) in communication with a memory element (10) containing a program code (11) including a power management module (12) which allows the bolus (1) to operate in the reticulorumen (5) of the ruminant animal (3) during the entire life span of the ruminant animal from birth to death or from birth to the end of the productive lifespan of the ruminant animal (3).

For the purposes of this invention the term "ruminant animal (3)" means any mammal of the suborder Ruminantia (both wild and domestic) and, without limiting the breadth of the foregoing definition, includes as illustrative examples: cattle, buffalo, goats, sheep, deer, antelope, giraffes, yaks, okapi, chevotain or the like.

For the purposes of this invention the term "birth" means the emergence of the ruminant animal (3) from the body of its mother to begin life as a physically separate ruminant animal (3).

For the purposes of this invention the term "death" means the permanent cessation of vital bodily functions to end life of a ruminant animal (3).

For the purposes of this invention the term "life span" means the period of time between birth and death of a ruminant animal (3).

For the purposes of this invention the term "productive lifespan" means the period of time between birth and the age reached before being culled from production.

For the purposes of this invention the term "reticulorumen (5)" means the first chamber in the alimentary canal of a ruminant animal (3) composed of the rumen and reticulum. The reticulum differs from the rumen with regard to the texture of its lining. The rumen wall is covered in small, finger-like projections called papillae, whereas the reticulum is lined with ridges that form a hexagonal honeycomb pattern. Despite the differences in the texture of the lining of the two parts of the reticulorumen (5), it represents one functional space.

The bolus (1) and the animal monitoring system (4) are described herein in terms of functional block components and various process steps. It should be appreciated that such functional blocks may be realized by any number of hardware or software components configured to perform the specified functions. For example, the bolus (1) and the animal monitoring system (4) may employ various integrated circuit components which function as: memory elements, processing elements, logic elements, look-up tables, or the like, which may carry out a variety of functions under the control of one or more processors or other control devices.

Figure 2:
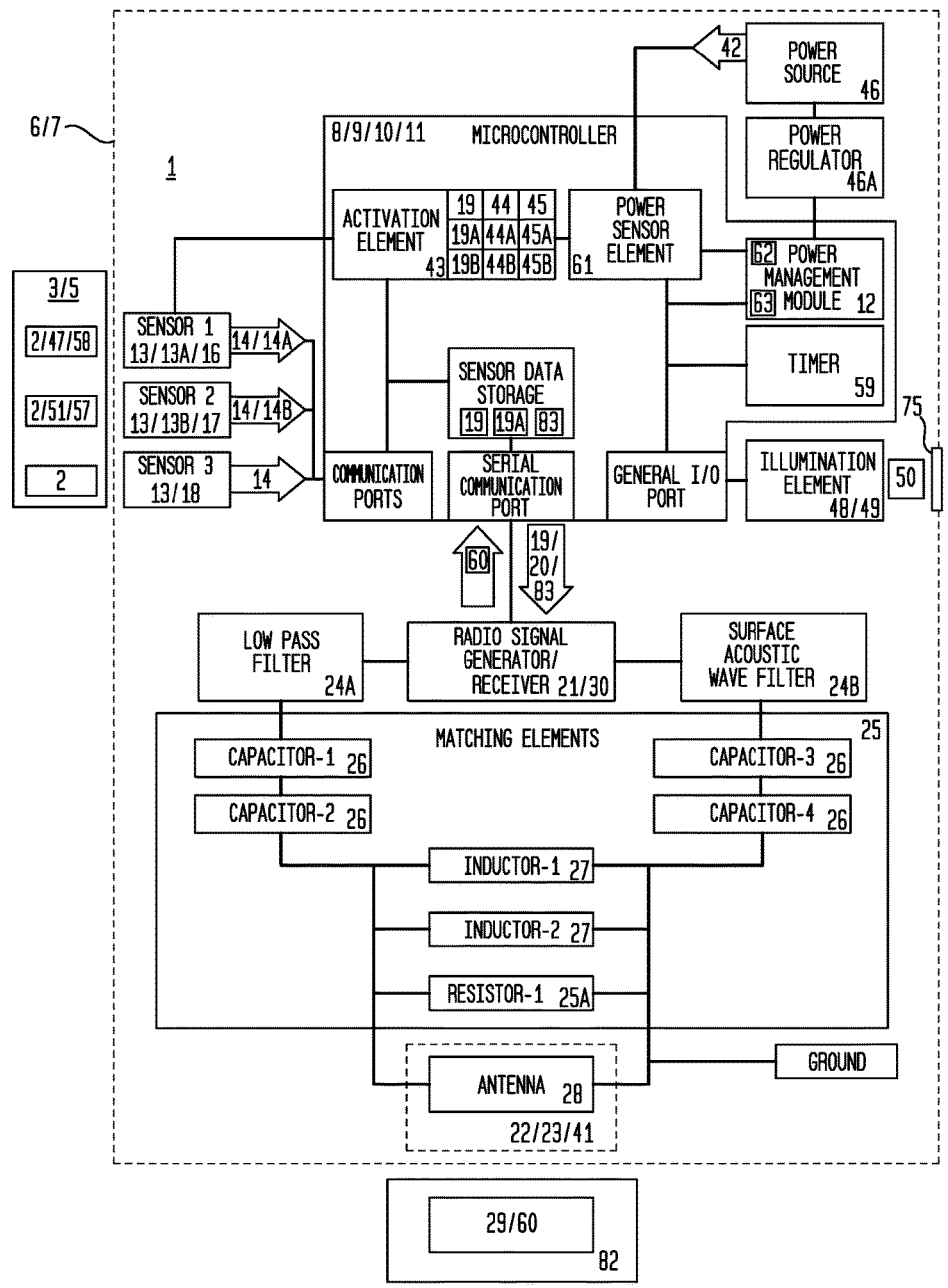
FIG. 2 is a block diagram of a particular embodiment of a bolus capable of being orally administered to a ruminant animal.

Now referring generally to FIG. 2, the bolus (1) can include one or more sensors (13) each capable of generating a sensor signal (14)(whether analog or digital) which varies based on a corresponding change the one or more physiological parameters (2) of a ruminant animal (3). For the purposes of this invention the term "physiological parameter" means a measurable condition of a ruminant animal (3), and without limitation to the breadth of the foregoing, includes one or more of: movement (including one or more of the pitch, yaw, roll, tilt, vibration, jolt, impact, or the like), temperature, sound (including one or more of reticulorumen digestive sounds, heartbeat sound, or the like), heart rate, or the like. Each of the one or more sensors (13) can generate a sensor signal (14) (whether analog or digital) which varies based upon occurrence or change in the sensed physiological parameter (2).

As illustrative examples, sensors (13) suitable for use in particular embodiments include: an omnidirectional tilt and vibration sensor (16)(also referred to as an "accelerometer") (PN SQ-SEN-200) distributed by Signal Quest Precision Microsensors; a temperature sensor (17) such as a Betachip Thermistor (PN 1K2OG3) distributed by BetaTHERM Sensors; a microphone (18) distributed by ST Microelectronics (PN MP34DT01); a humidity sensor (PN HCZ-D5) distributed by Ghitron Technology CO., Ltd; an ultra-miniature pressure transducer (PN COQ-062) distributed by Kulite, a proximity sensor (PN PY3-AN-3) distributed by Automation Direct.com, or similar or equivalent sensors. The illustrative examples and description of these sensors (13) are intended to provide a person of ordinary skill in the art sufficient information to make and use embodiments of the bolus including a numerous and wide variety of sensors whether or not specifically enumerated.

The microcontroller (8) includes a processor (9) in communication with the memory element (10) which contains a computer code (11). In part, the computer code (11) can be executed to continuously or intermittently transform the analog or digital sensor signal (14) from the one or more sensors (13) as encoded physiological data (19)(also referred to as "encoded sensor signals"). The encoded physiological data (19) varies based upon change in the sensor signal (14) which correspondingly varies based upon change in the sensed physiological parameter (2). As to particular embodiments, the computer code (11) can be executed to encode or recode from time to time an amount of sensor calibration data (19A) which allows calculation and output of a physiological parameter value (20) of the ruminant animal (3) (whether by the bolus (1) or by operation of a remote computer (82)). The computer code (11) can be further executed to couple animal identification data (83) to the encoded physiological data (19).

The computer code (11) can be further executed to control a radio signal generator (21), for example, an oscillator to generate a stable radio signal (22). An oscillator suitable for use with the invention is available from Freescale Semiconductor, Part No. MC1319x, MC1320x, MC1321x, and MC1322x, and similar or equivalent components. In regard to the particular embodiment of the invention, the radio signal generator (21) can generate a radio signal (22) having a radio signal frequency (23) between about 410 MHz and about 1 Gz. As one particular embodiment of the invention, the radio signal generator (21) can generate a radio signal frequency (23) of about 433 MHz. As to other particular embodiments, the radio signal generator (21) can generate a radio signal (22) having a radio signal frequency (23) of about between about 700 MHz to about 1 GHz. The radio signal frequency (23) can be selected from the group including or consisting of: between about 700 MHz to about 800 MHz, 750 MHz to about 850 MHz, about 800 MHz to about 900 MHz, about 850 MHz to about 950 MHz, and about 900 MHz to about 1 GHz.

The computer code (11) can further function to control a radio frequency stabilizer (24)(shown in the example of FIG. 2 as a low pass filter (24A) and a surface acoustic wave filter (24B)) which functions to offset changes in radio signal wave flux caused by changes in temperature or power to the radio signal generator (21). A radio frequency stabilizer (24)

suitable for use with embodiments is available from Hope Microelectronics Co., Ltd, Part No. HF433E, RF Monolithics, Inc., Part No. RF 1172C, and similar or equivalent parts.

Embodiments of the bolus (1) can further include matching elements (25) which function to match the input impedance of the electrical load or the output impedance of the loads corresponding signal source to maximize the power transfer or minimize signal reflection from the load. In an ideal situation, source impedance and load impedance should be equal to maximize power transfer.

Three elements influence the balance of impedance in radio design: the antenna (28) or "load", the radio signal generator (21) or "source", and the device's ground plane. Since each of these elements have different physical characteristics, their corresponding impedances are inherently different. The passive capacitors (26) and inductors (27) that make up the matching elements (25) of embodiments of the bolus (1) are used to mitigate these differences and rebalance the impedance for a given radio signal frequency (23).

Impedance for an inductor (27) is given by, $$Z = iwL$$

where L is the inductance and w is angular frequency. Impedance for a capacitor (26) is given by, $$Z = \frac{1}{iwC}$$

where C is capacitance
The reactance is, $$X = -\frac{1}{wC}$$

The matching elements (25) (also referred to as the "resonant circuit") include an array of inductors (27) and capacitors (26) used in series or in parallel to balance the circuit impedance once the impedance of the antenna (28), the radio signal generator (21), and the ground plane (not shown) are known.

A series resonant circuit (25) has an impedance that is the sum of the impedances of the inductor(s)(27) and capacitor(s)(26), $$Z = i\omega L + \frac{1}{i\omega C} = i\left(\omega L - \frac{1}{\omega C}\right)$$

The impedance of a Parallel Resonant Circuit is found as follows, $$Z = i\left(\frac{\omega L}{1 - \omega^2 LC}\right)$$

Resonance in the resonant circuit (25) occurs when the resonant circuit (25) is driven at a frequency w0 at which the inductive and capacitive reactances are equal in magnitude. The frequency at which this equality holds for the resonant circuit is called the resonant frequency, and can be determined, as follows, $$\omega_0 = \frac{1}{\sqrt{LC}}$$

This value can then be converted to hertz, $$f_0 = \frac{\omega_0}{2\pi} = \frac{1}{2\pi\sqrt{LC}}$$

The calculations above can be used to identify the inductors (27) and capacitors (26) used as matching elements (25) in association with the radio signal generator (21) that operates at a specific radio signal frequency (23) to balance the impedance between the radio signal generator (21) and the antenna (28) and limiting the bandwidth to eliminate interference. After the signal passes through the matching elements (25) the resistance of the circuit can be altered to ensure an industry standard of 50 Ohms resistance in the transmission line to the antenna (28). The resistance of the circuit can be altered by inclusion of resistor (25A) to establish the standard 50 Ohms resistance in the circuit.

These calculations, however, apply to a radio signal generator (21) used in normal atmospheric air (also known as "free air"). Because the radio signal generator (21) included in embodiments of the bolus (1) operate within the mass of a ruminant animal (3), it has been discovered that the center frequency (the arithmetic mean of the lower cutoff frequency and the upper cutoff frequency) is shifted lower and may not have the maximum gain.

Accordingly, there can be a substantial advantage, by selection of the inductors (27) and capacitors (26) as well as their position in the resonant circuit (25) to increase the inductance and capacitance values to purposefully shift the center frequency upward and allowing the radio signal frequency (23) to be re-tuned to a desired radio signal frequency (23) by passing through the mass of the ruminant animal (3).

Embodiments of the bolus (1) further include an antenna (28) which converts electric power into radio signal (22). In transmission, the radio signal generator (21) supplies an electric current oscillating at one of the above described radio signal frequencies (23). In reception, the antenna (28) intercepts some of the power of an electromagnetic wave (29) in order to produce a tiny voltage at its terminals that is applied to a receiver (30). As to particular embodiments, the antenna (28) can, but need not necessarily, be a laid down electrically conductive path on a printed circuit board (31). An advantage of this configuration of antenna (28) can be that it does not require winding upon or interaction with a magnetic field of a magnet to transmit the radio signal (22). Accordingly, this configuration of antenna (28) can produce a lesser amount of interference from a magnetic field of a magnet (69) contained in the bolus (1) resulting a lower incidence of loss of the radio signal (22) or less modulation of the radio signal (22) which results in a greater consistency (or lesser amount of lost data) in transmission of encoded physiological data (19) associated with the ruminant animal (3).

Now referring primarily to FIGS. 4 through 13, particular embodiments can, but need not necessarily, include an antenna (28) including a first electrically conductive loop (32) electrically interconnected to a second electrically conductive loop (33)(as shown in the example of FIGS. 6 through 13) electrically connected to the radio signal generator (21) or radio signal receiver (30)(or combined as a radio signal transceiver (21/30)). As to particular embodiments, the first or the second or the pair of electrically conductive loops (32)(33) can each include a conductive sheet material (or a laid down conductive path or conductive layer) having an inner annular edge (34) and an outer annular edge (35) which join opposed loop faces (36)(37). Typically, the conductive sheet material will be a copper sheet material or a copper layer. As to particular embodiments, the antenna (28) can further include a non-electrically conductive substrate (38) such as a circuit board (31) (as shown in the example of FIG. 6) disposed between the pair of electrically conductive loops (32)(33) with one or more vias (39) electrically interconnecting the first and second electrically conductive loops (32)(33) by one or more holes (40) through the non-electrically conductive substrate (38). The one or more holes (40) can be made electrically conductive by electroplating, or by lining the hole with a tube or a rivet thereby electrically interconnecting the pair of electrically conductive loops (32)(33). There can be substantial advantages in structuring the antenna (28) as above described and as shown in FIGS. 4 through 13. First, the structure increases the cross-section width of the antenna (28) which increases the stability of the radiated electrical field (41) of the antenna (28). Second, the structure increases the bandwidth of the antenna (28) allowing shift in radio signal frequency (23) or attenuation resulting from passing through the mass of the ruminant animal (3) to be more readily counteracted. Third, the structure alters the magnetic field and electrical field generation which reduces the impact of uncontrollable changes in the orientation of the bolus (1) and correspondingly the orientation of the antenna (28) in the reticulorumen (5) of the ruminant animal (3).

Figure 4:
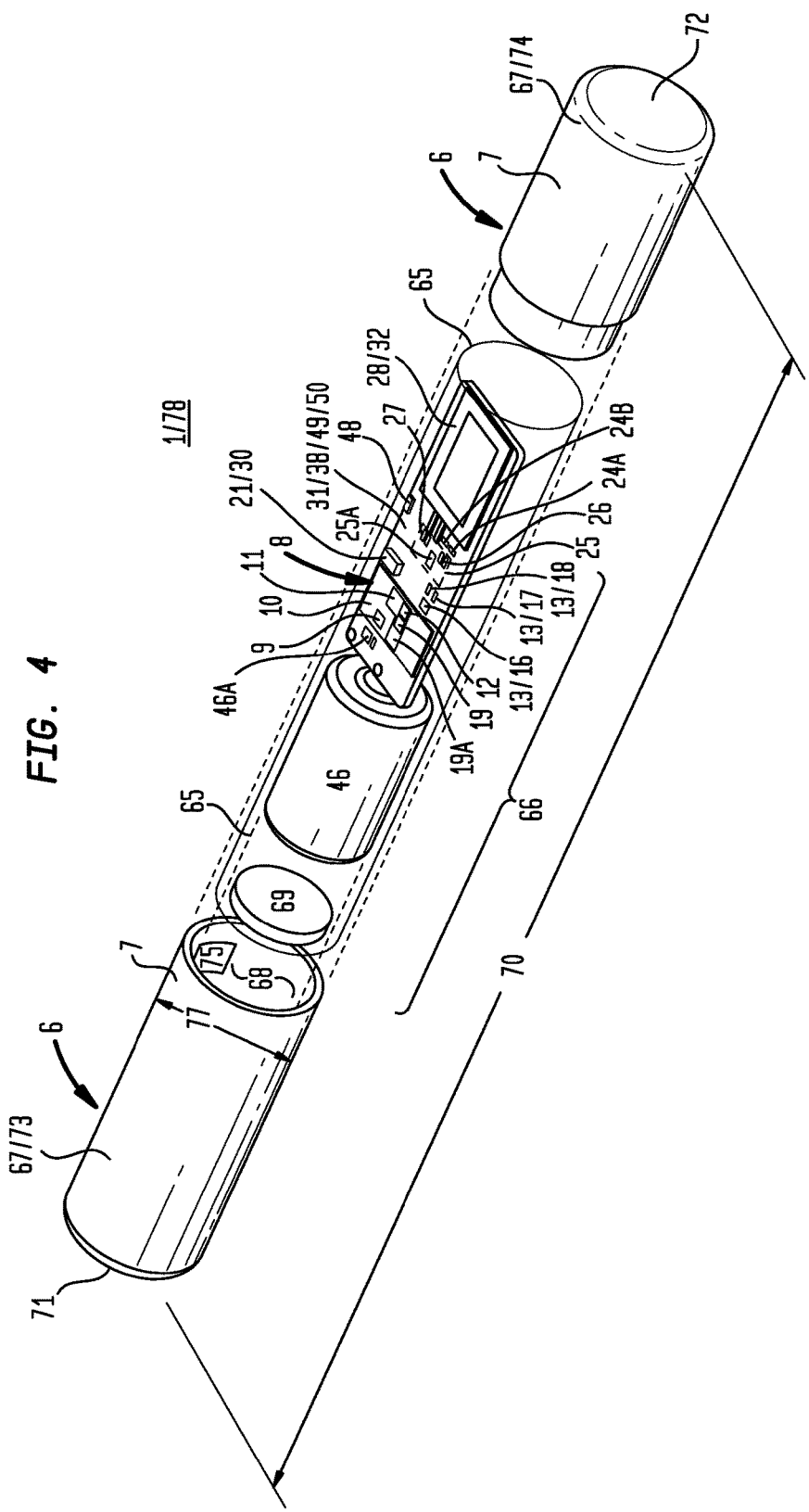
FIG. 4 is an exploded view of a particular embodiment of a bolus capable of being orally administered to a ruminant animal.
Figure 5:
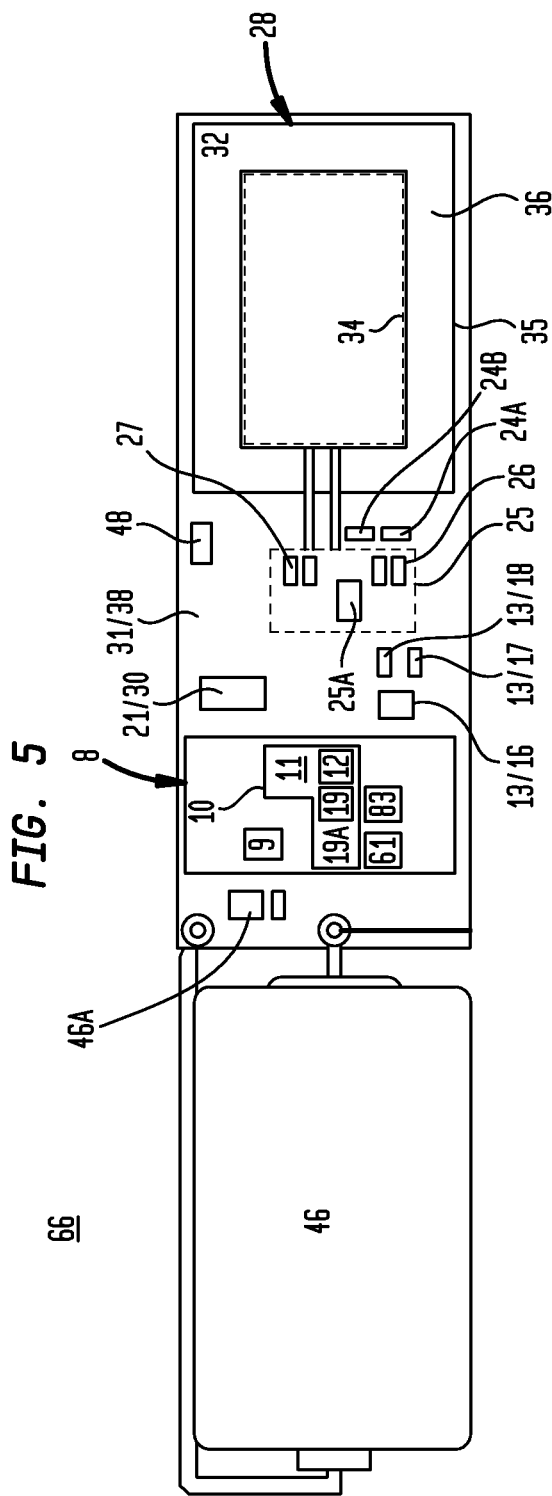
FIG. 5 is a diagram of a particular embodiment of the animal monitoring assembly of the bolus.

Again referring primarily to FIGS. 2, 4 and 5, embodiments of the bolus (1) further include a power source (46) (and associated power regulator (46A)) which supplies and adjusts energy (42) (electrical power) to the bolus (1). The power source (46) shown in FIGS. 2, 4 and 5 can take the form of a battery such as a AA battery, a AAA battery, or the like. The power source (42) provides power to the electronic components supported on the printed circuit board (31) including for example: the microcontroller (8), radio frequency generator (21) and one or more sensors (13). Because the power source (46) of a bolus (1) disposed in the reticulorumen (5) of the ruminant animal (3) cannot be recharged, the operational lifespan of bolus (1) will depend upon capacity of the power source (46) in ampere-hours (Ah) and the load current of the circuit. Power source (46) life will be longer as the load current is reduced and vice versa. The calculation to find out the capacity of power source (46) in the form of a battery can be mathematically derived from the following formula:

Battery Life=Battery Capacity in amps per hour/load current in amps×0.70

As to particular embodiments of the bolus (1), the computer code (11) can include a power management module (12) which functions to regulate energy use by the bolus (1) to extend the operational life of the bolus (1) disposed in the reticulorumen (5) of the ruminant animal (3). Embodiments of the bolus (1), including particular embodiments the power management module (12), can be operational within the reticulorumen (5) of the ruminant animal (3) for greater than three years and up to about ten years, a period of time substantially greater than that of conventional bolus.

As one illustrative example, embodiments of the inventive bolus (1) can be orally administered to a calf at, or immediately after birth, and remain operational over the entire productive lifespan (53) of the dairy cow, on average about 2.4 lactations, or about five to six years.

As another illustrative example, a ewe typically has a productive lifespan (53) of between about five years to about seven years of age. A ewe's productivity usually peaks between 3 and 6 years of age and begins to decline after the age of seven. As a result, most ewes are removed from a flock before they would reach their natural life expectancy. Accordingly, embodiments of the bolus (1) disposed in the reticulorumen (5) of the ewe at birth can be operational throughout the entire productive lifetime (53) of the ewe.

As to particular embodiments of the bolus (1), the power management module (12), can but need not necessarily include, an activation element (43) which functions to enable and encode the sensor signal(s)(14) from one or more sensors (13) and can further function to compare the one or more encoded sensor signals (19) against one or more preselected activation code(s)(44). If by comparison of the encoded sensor signal(s)(19) against the preselected activation code(s)(44), a pre-selected activation match threshold (45) is met, the activation element (43) can further function to cause activation of the bolus (1) for normal operation. This provides the advantage of avoiding inadvertent or premature activation of the bolus (1) and the corresponding unnecessary expenditure of energy (42) from the power source (46).

As one illustrative example of the function of the activation element (43), the bolus (1) can include a first sensor (13A) which can be an accelerometer (16). Accelerometers (16) in accordance with embodiments of the invention can sense the movement of the bolus (1)(whether within or without the ruminant animal), in a manner similar to accelerometers (16) used in tablet computers and digital cameras, such that images on display screens are always displayed upright, or as used in drones for flight stabilization. The accelerometer (16) can be enabled by the function of the activation element (43), and the activation element (43) can further function to encode the first sensor signal (14A) from the accelerometer (16) and compare the first encoded sensor signal (19A) against a first preselected activation code (44A). The first preselected activation code (44A), in the context of this illustrative embodiment, can correspond to a particular pre-activation movement (47) of the bolus (1) which can, but need not necessarily be, three serial reciprocal linear movements of the bolus (1) each terminating in an impact of the bolus (1) within a period of time of between about five seconds and ten seconds (also referred as "three bumps"). If the pre-activation movement (47) of the bolus (1) including "three bumps" meets the first pre-selected activation match threshold (45A) relating to the first preselected activation code (44A) corresponding to "three bumps" the activation element (43) can cause the bolus (1) to be activated for normal monitoring of the ruminant animal (3). As to particular embodiments, the bolus (1) can, but need not necessarily, include an illumination element (48), such as a light emitting diode (49). The illumination element (48) can be switched on by operation of the activation element (43) to provide an amount of light (50) as an indicator that the bolus (1) has been activated and can be orally administered to a ruminant animal (3).

As to particular embodiments, the bolus (1) can, but need not necessarily, include a second sensor (13B) which can be a temperature sensor (17) (also referred to as a "thermistor"). Thermistors (17), in accordance with embodiments of the invention, can sense the temperature (57) of the bolus (1)(whether within or without of the ruminant animal) in a useful range of temperature and accuracy depending upon the ruminant animal (3) into which the bolus (1) is to be orally administered and the determinations to be made from the sensed temperature (57). For example, the useful temperature range in dairy cow will be between about 95° F. (about 35° C.) to about 115° F. (about 46° C.) with an accuracy of between about 0.1° C. and about 0.3° C. The normal temperature of an adult cow will typically be about 101.5° F. (about 38.5° C.), but can vary throughout the estrous cycle with the lowest temperature being just before heat and highest temperature on the day of heat or due to being in milk, and a temperature of about 103.0° F. (about 39.4° C.) to about 104.0° F. (about 40° C.) and upward to about 108° F. (about 42.2° C.), typically indicative of a sick cow. However, this illustrative example is not intended to preclude the use of thermistors (17) which may sense a wider temperature range, as one illustrative example, about −40° C. to about +125° C., as long as the accuracy is not less than about 0.1° C. to about 0.2° C. of the actual temperature about the bolus (1) and the time constant to change from one temperature value to another temperature value is sufficiently short to support the sampling rate of the sensor signal (14) effected by the computer code (11) in regard to the thermistor (17). For example, thermistors (17) utilized with embodiments of the bolus (1) may have a time constant of about one minute or less and while the sampling rate may be once every 10 minutes to 20 minutes or longer depending upon the application.

As to particular embodiments, the activation element (43) having activated the bolus (1)(and as to particular embodiments, switched on the light illumination element (48)) can, but need not necessarily, further enable and encode a second sensor signal (14B) from a second sensor (13B) which can be a thermistor (17). The activation element (43) can further function to encode the second sensor signal (14B) from the second sensor (13B) such as thermistor (17) and compare the second encoded sensor signal (19B) against the second preselected activation code (44B). The second preselected activation code (44B), in the context of this illustrative embodiment, can correspond to a pre-activation temperature (51) of the bolus (1) which can, but need not necessarily be, three serial temperature reads of the bolus (1) each about 15 minutes apart within a period of time of about 45 minutes (also referred to as "three temperature reads"). If the pre-activation temperature (51) of the bolus (1) including "three temperature reads" meets the second pre-selected activation match threshold (45B) for the second preselected activation code (44B) corresponding to "three temperature reads" the activation element (43) can cause the bolus (1) to be activated for normal monitoring of a ruminant animal (3). In the illustrative example of a bolus (1) used in calves or cows, if the three temperature reads are between about 100° F. (about 37.8° C.) and about 105° F. (about 40.6° C.), this would be indicative that the bolus (1) resides in the reticulorumen (5) of a calf or cow, and the activation element (43) can then function to cause the bolus (1) to be activated for normal monitoring of the ruminant animal (3). This provides the advantage of avoiding inadvertent or premature activation of the bolus (1) and the corresponding unnecessary expenditure of energy (42).

As to particular embodiments, the power management module (12) can, but need not necessarily, further function to reconfigure the mode of operation of the bolus (1) or allow the mode of operation of the bolus (1) to be reconfigured while residing in the reticulorumen (5) of the ruminant animal (3) to regulate energy (42) use by the bolus (1) which can have the advantage of extending the operational life of the bolus (1).

As to particular embodiments, the power management module (12) can regulate energy (42) use by the bolus (1) by enabling or disabling one or more sensors (13) based upon a pre-determined set of physiological parameters (2) to be sensed during one or more stages (52) in a lifespan (53) of the ruminant animal (3). The encoded physiological data (19) useful in making determinations relating to a ruminant animal (3) may be different in a first stage (54) in the lifespan (53)(for example, the time period between birth and puberty) as compared to a second stage (55) (for example, the time period commencing with puberty until the end of reproductive age (or useful reproductive age)) (as shown in the example of FIG. 1). As one illustrative example in dairy cows, from birth until puberty in dairy cows at about eight months to about seventeen months of age depending upon the breed, the useful encoded physiological data (19) may only include encoded physiological data (19) relating to temperature (57). Accordingly, in a first stage (54) of the ruminant animal (3) lifespan (53) the power management module (12) can function upon activation of the bolus (1), as above described, to only enable and periodically read the sensor signal (14A) and generate encoded physiological data (19) for temperature (57) of the ruminant animal (3). Additionally, because the encoded physiological data (19) for temperature (57) may only be used to determine whether the ruminant animal (3) is sick, there may be a substantial period of time between reads of the temperature sensor signal (14), such as, once in a twenty-four hour period. Similarly, there may be a substantial period of time between operational periods of the radio signal generator (21), such as twenty four hours, and the operational period of the radio signal generator (21) may be very short, such as, a few milliseconds (also referred to as a "transmission burst (56)"). Because the majority of energy (42) used by the bolus (1) is in operation of the radio signal generator (21), increasing the time period between transmission bursts (56) and limiting the duration of the transmission burst (56) only to that period of time necessary to transmit the limited amount of encoded physiological data (19) can substantially increase the operating lifespan of the bolus (1).

By comparison, in second stage (55) of the lifespan (53) of a ruminant animal (3) from puberty to the end of reproductive age of the ruminant animal (3), the useful encoded physiological data (19) may include both encoded physiological data (19) for temperature (57) and encoded physiological data (19) for movement (58). As above explained, the temperature (57) of ruminant animal (3) may vary throughout the estrous cycle with the lowest temperature being just before heat and highest temperature on the day of heat. Additionally, the activity of the cow can measurably change prior to or concurrent with heat.

Accordingly, as to particular embodiments, the power management module (12) can further include a timer element (59) which functions to assess elapsed time from activation of the bolus (1) allowing regulation of energy (42) use by the bolus (1) based on elapsed time which can be coordinated to one or more of the stages (52) in the lifespan (53) of the ruminant animal (3). As one illustrative example, if the bolus (1) is orally administered at birth, the timer element (59) and the power management module (12) can function to enable a first sensor (13A) (or first set of sensors (13) providing useful encoded physiological data (19) during the first stage (54)) and encode physiological data (19) for temperature (57) (or first set of physiological parameters)

for a period of time corresponding the first stage (54) of the lifespan (53) of the ruminant animal (3)(for example, between birth and puberty), and then function to further enable a second sensor (13B)(or second set of sensors (13) providing useful encoded physiological data (19) during a second stage (55) of the ruminant animal (3)) and encode physiological data (19) for both temperature (57) and movement (58).

Additionally, because the encoded physiological data (19) for movement (58) and temperature (57) may be used to determine whether the ruminant animal (3) is in estrus, the power management module (12) can function to reduce the period of time between reads of the sensor signal (14) temperature (57) and the sensor signal (14) for movement (58), such as, four times in a twenty-four hour period. Similarly, there may be a lesser period of time between operational periods of the radio signal generator (21), such as every six hours, and the operational period of the radio signal generator (21) may be adjusted to a period of time to transmit the additional encoded physiological data (19).

As to particular embodiments, once the ruminant animal (3) becomes pregnant and during the pregnancy, the power management module (12) can further function to reconfigure the operation of the bolus (1) to disable the sensor (13) for movement (58) and read only the sensor (13) for temperature (57) and transmit encoded physiological data (19) at less frequent intervals.

As to particular embodiments, the program code (11) can be reprogrammed while the bolus (1) resides in the reticulorumen (5) of the ruminant animal (3) by receiving programming data (60) to reconfigure the power management module (12) to regulate energy (42) use by the bolus (1), as above described.

As to particular embodiments, the power management module (12) can, but need not necessarily, include a power sensor element (61) executable to determine the remaining amount of energy (42) in the power source (46). The power management module (12) can be further executed to determine the amount of energy (42) required to power the bolus (1) through a pre-determined period of time (62) based on the then existing program code (11) contained in the memory element (10) of the bolus (1). The power management module (12) can be further executed to compare the remaining amount of energy (42) in the power source (46) with the amount of energy (42) required to power the bolus (1) through the pre-determined period of time (62) based on the then existing program code (11) to determine the difference in the amount of energy (42) remaining in the power source (46) and the amount of energy (42) required to power the bolus (1) through the pre-determined period of time (62). The power management module (12) can be further executed to perform one or more power regulation events (63) to make up the difference in the amount of energy (42) to allow operation of the bolus (1) through the pre-determined period of time (62). The power regulation events (63) can include or consist of one or more of: switching off the light illumination element (48), increasing the interval of time between operation of the radio signal generator (21), decreasing the operational time period of the radio signal generator (21), disabling one or more of the plurality of sensors (13), interrupt encoding of the sensor signal (14) from one or more of said plurality of sensors (13), or other re-programming that reduces energy (42) use.

As to particular embodiments, the power management module (12) can be pre-programmed to perform one or more of the power regulation events (63) in one or more pre-programmed priority orders based upon the magnitude of the difference in the amount of energy (42) remaining in the energy source (46) and the required amount of energy (42) to power the bolus through the remaining portion of a pre-programmed or re-programmed life cycle. Alternately, the power management module (12) can function to encode and transmit as part of a transmission burst (56) encoded power source data (64) from which the remaining amount of energy (42) in the energy source (46) can be calculated using a remote specialized computer (82) and the power management module (12) can be re-programmed to execute one more power regulation events (63) based on a priority order encoded in the programming data (60) received by the bolus (1).

Now referring primarily to FIGS. 4 and 5, embodiments of the bolus (1) which are orally administered to a ruminant animal (3) can, but need not necessarily, include an inert bolus body (6) having external dimensional relations adapted to allow oral administration and retention of the bolus (1) in the reticulorumen (5) of a ruminant animal (3). As one non-limiting example, the inert bolus body (6) can include an amount of plastic resin (65) cast about the animal monitoring assembly (66) ("AMA"), including one or more of the components above-described. The amount of plastic resin (65) can be, as an example, a plastic resin such as urethane resin, epoxy resin, polyester resin, or the like used in accordance with the manufacturer's instructions. As to other embodiments, the inert bolus body (6) can comprise a sealable housing (67) defining a hollow inside space (68) which receives the AMA (66). As to other embodiments, the sealable housing (67) including the AMA (66) received in the hollow space (68) (and as to particular embodiments further including one or more magnets (69) received in the hollow space (68)) can have the amount of plastic resin (65) cast about the AMA (66) (and one or more magnets (69)) located inside said sealable housing (67).

Again referring primarily to FIG. 4, configurations of the inventive bolus (1) suitable for oral administration to a ruminant animal (3) can have a generally cylindrical configuration with a diameter (77) in orthogonal cross section in the range of about one-half inch (about 13 millimeters ("mm")) to about one and one quarter inch (about 32 mm) and having a bolus length (70) disposed between a first bolus end (71) and a second bolus end (72) in the range of about two inches (about 50 mm) and about five inches (about 127 mm). Particular embodiments of the bolus (1) can have a length of about four inches (about 102 mm) and a diameter (77) in orthogonal cross section of about one inch (about 25 mm). While the example of FIG. 4 shows the bolus (1) including a housing (67) having matable halves (73)(74) with an outer most external surface (7) configured as a cylinder; the bolus (1) can have numerous and varied outer most external surface (7) configurations capable of oral administration and retention within the reticulorumen (5) of a ruminant animal (3). The inert bolus body (6) can be molded, cast, or machined from biocompatible (or biologically inert) non-magnetic materials which allow transmission of the radio signal (22) from within the bolus (1) to outside of the ruminant animal (3). As examples, the inert bolus body (6) can be made from plastics such as nylon, fluorocarbon, polypropylene, polycarbonate, urethane, epoxy, polyethylene, or the like; or metals such as stainless steel; or other materials such as glass can be utilized. The bolus (1) having a hollow inside space (68) can be generated by a wide variety of procedures such as molding, casting, fabrication or the like. As one non-limiting example, a cylindrical tube having an external diameter and an internal diameter, as above described, can be divided into sections of suitable length to which end caps can be fitted. Alternately, a bore can be made in a cylindrical solid rod having an external diameter, as above described, to provide a closed end tube with the bore having sufficient dimension to provide the hollow inside space (68).

As to particular embodiments, the inert bolus body (6) can, but need not necessarily, include a translucent or transparent element (75) to allow viewing of the amount of light (50) generated by the illumination element (48) as a viewable indicator that the bolus is activated as above described. The translucent or transparent element (75) can include a portion or the entirety of the housing (67) of the inert bolus body (6).

As to particular embodiments of the bolus (1), the inert bolus body (6) can be configured for oral administration to ruminant animals (3) at birth. The digestive track between the mouth (76) and the reticulorumen (5) of a ruminant animal (3) at birth can have comparatively restrictive dimensions as compared to adult ruminant animals (3). Therefore, conventionally configured bolus (1) may not be orally administered to ruminant animals (3) at birth or when orally administered may cause injury or be regurgitated as the digestive track between the mouth (76) and the reticulorumen (5) enlarges due to growth of the ruminant animal (3).

The configuration of outer most external surface (7) of the housing (67) of the inert bolus body (6) or the bolus density (78), or combinations thereof, can be critical when a bolus (1) is orally administered to a ruminant animal (3) at birth. It has been discovered that while the bolus length (70) between the first and second bolus ends (71)(72) can be more variable, it can be critical that the greatest bolus diameter (77) (or width) of the outer most external surface (7) along the length (70) between the pair of bolus ends (71)(72) should be between one half inch (about 13 mm) and not exceed three quarters of an inch (about 19 millimeters). The configuration of the outer most external surface (7) of the bolus (1) can have a bolus width (77) selected from the group including or consisting of: about 13 mm to about 15 mm, about 14 mm to about 16 mm, about 15 mm to about 17 mm, about 16 mm to about 18 mm, and about 17 mm to about 19 mm.

As one illustrative example, a bolus (1) configured for oral administration to ruminant animals (3) at birth can have an outer most external surface (7) of the bolus body (6) having cylindrical configuration as shown in the example of FIG. 4. The bolus length (70) can vary between about three inches (about 76 mm) and about six inches (about 152 mm) between the a pair of bolus ends (71)(72); however, the outer most external surface (7) at any cross section orthogonal to the bolus length (70) should not exceed about 19 millimeters. As a second illustrative example, the bolus body can be substantially spherical having an external diameter not exceeding about three quarters of an inch (about 19 mm).

Embodiments of the inventive bolus (1) can, but need not necessarily, have a bolus density (78) of between about 2.1 grams per cubic centimeter ("$g/cm^3$") to about 3.3 $g/cm^3$. However, there can be substantial advantages in configuring the bolus (1) to achieve a bolus density (78) in the range of between about 2.1 $g/cm^3$ to about 3.3 $g/cm^3$ in that the bolus (1) is substantially less likely to be regurgitated or ejected from reticulorumen (5) of a ruminant animal (3) as compared to conventional bolus. It can be critical to achieve a bolus density (78) of between about 2.1 $g/cm^3$ to about 3.3 $g/cm^3$ when dimensions of the outer most external surface (7) are reduced for oral administration to ruminant animals (3) at birth or the bolus (1) resides in the reticulorumen (5) of the ruminant animal (3) for the entire lifespan (53) of the ruminant animal (3). Within the range of bolus density (78), the bolus density can be selected from the group including or consisting of: about 2.3 $g/cm^3$ to about 2.5 $g/cm^3$, about 2.4 $g/cm^3$ to about 2.6 $g/cm^3$, about 2. $g/cm^3$ to about 2.7 $g/cm^3$, about 2.6 $g/cm^3$ to about 2.8 $g/cm^3$, about 2.7 grams $g/cm^3$ to about 2.9 $g/cm^3$; about 2.8 $g/cm^3$ to about 3.0 $g/cm^3$, about 2.9 $g/cm^3$ to about 3.1 $g/cm^3$; about 3.0 $g/cm^3$ to about 3.2 $g/cm^3$, and about 3.1 $g/cm^3$ to about 3.3 $g/cm^3$.

Figure 3:
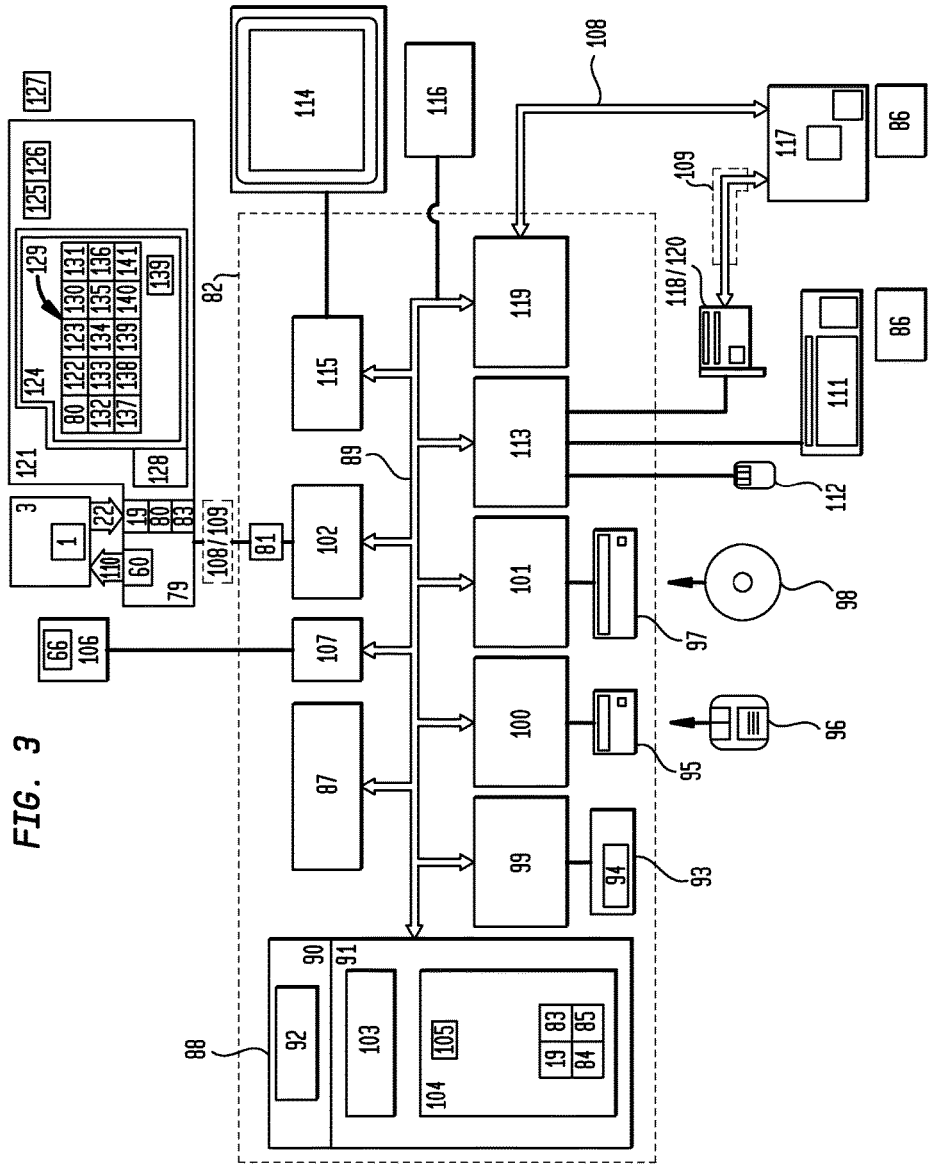
FIG. 3 is a block diagram which shows a particular embodiment of an animal monitoring system including a specialized computer, a radio frequency reader and a bolus.

Now referring primarily to FIG. 3, the animal monitoring system (4) can, but need not necessarily, include one or more radio signal reader(s) (79) can be located to receive the radio signal (22) carrying the encoded physiological data (19) from one or more bolus (1). As to particular embodiments, the one or more radio signal readers (79) ("RSR") can further operate to assemble the encoded physiological data (19) into one or more data packets (80) which can be transmitted and received by a wired or wireless reception device (81) (which can be integrated into a specialized computer (82)). The reception device (81) can transfer the data packets (80) to a specialized computer (82). The specialized computer (82) can operate to transform the encoded animal identification data (83) and encoded physiological data (19) to output an animal identification value (84) (an alpha or numeric or other animal identifier) and to output physiological parameter values (85)(an alpha or numeric or other symbols). A computer user (86) can access the animal identification value (84) and the physiological parameter values (85) by use of the specialized computer (82).

Now referring generally to FIG. 3, the specialized computer (82) is described herein in terms of functional block components, screen shots, and various process steps. It should be appreciated that such functional blocks may be realized by any number of hardware or software components configured to perform the specified functions.

Similarly, the software elements of the present invention may be implemented with any programming or scripting language such as C, C++, JAVA, COBOL, ASSEMBLER, PERL, LABVIEW, or any graphical user interface programming language, extensible markup language (XML), Microsoft's VISUAL STUDIO.NET, VISUAL BASIC, or the like, with the various algorithms or Boolean Logic being implemented with any combination of data structures, objects, processes, routines or other programming elements. Further, it should be noted that the present invention might employ any number of conventional wired or wireless techniques for data transmission, signaling, data processing, network control, and the like.

It should be appreciated that the particular computer implementations shown and described herein are illustrative of the invention and its best mode and are not intended to otherwise limit the scope of the present invention in any way. Indeed, for the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a computer implemented animal monitoring system (4).

As will be appreciated by one of ordinary skill in the art, the present invention may be embodied in the alternative as a method, a data processing system, a device for data processing, a computer program product, or the like.

Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, ROM, flash RAM, or the like.

It will be understood that each functional block of the block diagrams and the flowchart illustrations, and combinations of functional blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of elements for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware based computer systems which perform the specified functions or steps, or suitable combinations of special purpose hardware and computer instructions.

Again referring to FIG. 3, the computer implemented animal monitoring system (4) can include a specialized computer (82) for receiving, processing and transforming a radio signal (22) from a reception device (81) carrying animal identification data (83) and animal physiological parameter data (19) to generate animal identification values (84) and physiological parameter values (85) accessible by the computer user (86). The specialized computer (82) can include at least one processing unit (87), a memory unit (88), and a bus (89) which operably couples components of the computer (82), including, without limitation the memory unit (88) to the processing unit (87). The computer (82) may be a conventional computer, a distributed computer, or any other type of computer which may contain all or a part of the elements described or shown to accomplish the functions described herein; the invention is not so limited. The processing unit (87) can comprise without limitation one central-processing unit (CPU), or a plurality of processing units which operate in parallel to process digital information, or a digital signal processor (DSP) plus a host processor, or the like. The bus (89) can be without limitation any of several types of bus configurations such as a memory bus or memory controller, a peripheral bus, and a local bus using any of a variety of bus architectures. The memory element (88) can without limitation be a read only memory (ROM) (90) or a random access memory (RAM)(91), or both. A basic input/output system (BIOS)(92) containing routines that assist transfer of data between the components of the specialized computer (82), for example during start-up, can be stored in ROM (90). The computer (82) can further include a hard disk drive (93) for reading from and writing to a hard disk (94), a magnetic disk drive (95) for reading from or writing to a removable magnetic disk (96), and an optical disk drive (97) for reading from or writing to a removable optical disk (98) such as a CD ROM or other optical media.

The hard disk drive (93), magnetic disk drive (95), and optical disk drive (97) and the reception device (81) can be connected to the bus (89) by a hard disk drive interface (99), a magnetic disk drive interface (100), and an optical disk drive interface (101), and a radio signal reception device interface (102), respectively. The drives and their associated computer-readable media provide nonvolatile storage of computer-readable instructions, data structures, program modules and other data for the computer (82). It can be appreciated by those skilled in the art that any type of computer-readable media that can store data that is accessible by a computer, such as magnetic cassettes, flash memory cards, digital video disks, Bernoulli cartridges, random access memories (RAMs), read only memories (ROMs), RFID devices or the like, may be used in the exemplary operating environment.

The computer (82) can further include an operating system (103) and an animal monitoring program (104)("AMP") which as to particular embodiments of the invention can include an animal monitoring assembly encoder-decoder module (105) ("AMA encoder-decoder") for programming the animal monitoring assembly (AMA)(66) with animal identification data (83). As to particular embodiments, programming of the AMA (66) can be accomplished using an animal monitoring assembly programmer (106) connected to the bus (89) by an AMA interface (107). The AMA encoder-decoder module (105) can be stored on or in the hard disk (94), magnetic disk (96), optical disk (98), ROM (90), in RAM (91) of the specialized computer (82) or alternately the functionalities of the AMA encoder-decoder module (105) may be implemented as an application specific integrated chip (ASIC) or file programmable gate array (FPGA), or the like.

As to particular embodiments, the specialized computer (82) can be further configured to generate programming data (60) based on computer user (86) interaction the AMP (104) which can be received by the RSR (79) over a local area network (108) over a wide area network (109). The RSR (79) can generate a second radio signal (110) to carry the programming data (60) to the radio signal receiver (30) contained in the AMA (66). The second radio signal (110) can be processed by the microcontroller (8) to reprogram the program code (11) and particularly the power management module (12) to correspondingly alter the operation of the AMA (66), regardless as to whether the bolus (1) containing the AMA (66) has a location outside of the ruminant animal (3) or has a location inside of the ruminant animal (3).

The computer user (86) can enter commands and information into the computer (82) through input devices such as a keyboard (111) and a pointing device (112) such as a mouse. Other input devices (not shown) may include for example: touch on a touch screen, a microphone, joystick, game pad, satellite dish, scanner, magnetic strip of a card, or the like. These and other input devices are often connected to the processing unit (87) through a serial port interface (113) that can be coupled to the bus (89), but may be connected by other interfaces, such as a parallel port, game port, or a universal serial bus (USB). A monitor (114) or other type of display device can also be connected to the bus (89) via interfaces such as a video adapter (115), or the like. In addition to the monitor (114), the computer (82) can further include peripheral output devices (116), such as speakers and printers.

The computer (82) may operate in a networked environment using logical connections to one or a plurality of remote second computers (117). These logical connections can be achieved by a communication device (118) coupled to or a part of the computer (82). Each of the plurality of remote second computers (117) can include a part or all of the elements as included in the specialized computer (82) although only a single box has been illustrated in FIG. 3 for the remote second computer (117).

When used in a LAN (108) networking environment, the computer (82) can be connected to the LAN (108) through a network interface (119). When used in a WAN (109)-networking environment, the computer (82) typically includes a modem (120), or other type of communications device, for establishing communications over the WAN (109), such as the Internet. The modem (120), which may be internal or external to the specialized computer (82), can be connected to the bus (89) via the serial port interface (113). In a networked environment, the AMP (104), or portions thereof, may be stored in any one or more of the plurality of remote second computers (117). It is appreciated that the logical connections shown are exemplary and other hardware elements and communications elements can be utilized for establishing a communications link between the specialized computer (82) and one or more of the a plurality of remote second computers (117).

While the computer elements and the network elements shown in FIG. 3 can be utilized to practice the invention including the best mode, it is not intended that the description of the best mode of the invention or any preferred embodiment of the invention be limiting with respect to the utilization of a wide variety of similar, different, or equivalent computer elements or network elements to practice embodiments of the invention which include without limitation hand-held devices, such as personal digital assistants or camera/cell phone, tablet or slate computers, multiprocessor systems, microprocessor-based or programmable consumer electronics, network PCs, minicomputers, mainframe computers, PLCs, or the like.

Now referring primarily to FIGS. 1 and 3, the RSR (79) can receive the first radio signal (22) from the AMA (66) inside the bolus (1) whether inside or outside of the reticulorumen (5) of the ruminant animal (3). The AMA (66) within the bolus (1) can send encoded animal identification data (83) and the encoded physiological data (19) using the first radio signal (22), as above described.

One illustrative embodiment of the RSR (79) as shown in FIGS. 1 and 3, provides a reader microcontroller (121) which includes a reader processor (122) which controls the functions of a variety of reader processor elements (123) stored in a reader memory element (124) each of which provides a response to events related to receiving the first radio signal (22) from the AMA (66) within the bolus (1) carrying encoded animal identification data (83) and encoded physiological data (19), or receiving reader sensor signals (125) from reader sensors (126) which monitor environmental parameters proximate the RSR (79) such as ambient temperature (127); or generating data packets (80) which include all or parts of such information, or sending data packets (80) to the computer (82) or a remote second computer (117) for access by a computer user (86). A reader microcontroller (121) suitable for use with embodiments of the RSR (79) can be obtained from Microchip Technology. Inc., 2355 West Chandler Blvd., Chandler, Ariz., Part No. PIC18F4620-I/PT, or similar or equivalent components can be suitable as a reader microcontroller (121) programmable to perform the above-described functions of the RSR (79).

Again referring primarily to FIG. 3, a reader antenna (128) can receive encoded animal identification data (83) and encoded physiological data (19) and other information generated by operation of the AMA (66) within the bolus (1) within or without of the ruminant animal (3). The reader antenna (128) can be tuned to the first radio signal (22) generated by the AMA (66).

Again referring primarily to FIG. 3, the reader sensor (126) can be located to sense the ambient temperature (127) surrounding the RSR (79). The reader sensor (126) can take the form of a thermistor. A suitable thermistor for use in embodiments of the RSR (79) is available from Microchip Technology, Inc., 2355 West Chandler Blvd., Chandler, Ariz., Part No. MCP98242, and similar and equivalent parts.

The reader sensor (126) can be operated under the control of a second reader processor (129) which functions to regulate power to the reader sensor (126) and converts the reader sensor signal (125) into a digital representation of the ambient temperature (127). The second reader processor (129) can further function to encode or re-encode from time to time an amount of reader temperature calibration data (130) which allows calculation and output of an ambient temperature value (131).

Again referring primarily to FIG. 3, a reader clock element (132) can operate under the control of a third reader processor element (133) to generate a date and time signal (134) that represents a date and time value (135).

Again referring primarily to FIG. 3, a fourth reader processor element (136) can function to assemble data packets (80) which as an example can include a representation of the ambient temperature value (141) and the date and time value (135) at which the information from the AMA (66) was received by the RSR (79). The assembled data packet (80) can be stored and retrieved from the reader memory element (124) under the control of the fourth reader processor element (136).

Again referring primarily to FIG. 3, a fifth reader processor element (137) can function to provide an ether net interface (138) for an ether net controller (139) to receive instructions or requests from the computer (82) (or remote computer (117). The fifth reader processor (137) can further function to operate a second radio signal generator (140) and transmit the second radio signal (110) to reprogram the computer code (11) or the power management module (12) of the AMA (66) within the bolus (1). The fifth reader processor element (137) can further function to send the data packets (80) to the ether net controller (139) for transmission to the computer (82).

As can be easily understood from the foregoing, the basic concepts of the present invention may be embodied in a variety of ways. The invention involves numerous and varied embodiments of a reciprocally telescoping door stop and methods for making and using such door stops including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "generator" should be understood to encompass disclosure of the act of "generating"—whether explicitly discussed or not—and, conversely, were there effectively disclosure of the act of "generating", such a disclosure should be understood to encompass disclosure of a "generator" and even a "means for generating." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the bolus or animal monitoring systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of monitoring the physiological parameters of a ruminant animal, comprising:
    disposing a bolus in the reticulorumen of said ruminant animals;

enabling or disabling one or more sensors in said bolus by execution of a computer code contained in a non-transitory computer readable media communicatively coupled to a processor, said enabling or disabling of said one or more sensors coordinated with a plurality of life stages in a lifespan of said ruminant animal;

generating a sensor signal from said one of more sensors when enabled, where said sensor signal varies based on a corresponding change in one or more physiological parameters of said ruminant animal; and transmitting encoded physiological data indicative of the physiological parameters of said ruminant animal.

2. The method of claim 1, wherein the step of enabling or disabling one or more sensors in said bolus is performed by operation of a power management module based upon a comparison of the sensor signal to a pre-determined set of one or more physiological parameters during said plurality of life stages in said lifespan of said ruminant animal.

3. The method of claim 1, wherein the step of enabling or disabling one or more sensors in said bolus further comprises assessing elapsed time from an activation of said bolus.

4. The method of claim 1, wherein said plurality of life stages in said life span of said ruminant animal comprise a first life stage prior to puberty and a second life stage commencing with puberty.

5. A method of monitoring physiological parameters of a ruminant animal, comprising:
generating a sensor signal from one or more sensors contained in a bolus orally administered to said ruminant animal, said sensor signal varies based on a corresponding change in one or more physiological parameters of said ruminant animal;

encoding said sensor signal from said one or more sensors as encoded physiological data corresponding to said one or more physiological parameters of said ruminant animal; and storing said encoded physiological data in a non-transitory computer readable media, enabling a radio signal generator located within said bolus;

activating said radio signal generator at pre-determined intervals to generate a radio signal to carry said encoded physiological data; and generating said radio signal having a frequency of between about 700 MHz to about 1 GHz.

6. The method of claim 5, wherein said frequency is selected from the group consisting of: between about 700 MHz to about 800 MHz, 750 MHz to about 850 MHz, about 800 MHz to about 900 MHz, 850 MHz to about 950 MHz, 900 MHz to about 1 GHz.

7. The method of claim 6, wherein said bolus further comprises matching elements which adjusts said frequency of said radio signal to compensate for a change in said frequency of said radio signal due to passing through a mass of said ruminant animal.

8. A method of monitoring physiological parameters of a ruminant animal, comprising:
determining a remaining amount of energy stored in a power source located within a bolus orally administered to said ruminant animal;

determining an amount of energy required by said bolus to operate through a pre-determined period of time based on current programming of a computer code contained in a non-transitory computer readable media contained in said bolus;

comparing said amount of energy required by said bolus to operate through said pre-determined period of time to said remaining amount of energy stored in said power source; and calculating a difference in said amount of energy remaining in the power source and said amount of energy required by said bolus to operate through said pre-determined period of time; and performing one or more power regulation events to offset said difference in said amount of energy remaining in the power source and said amount of energy required by said bolus to operate through said pre-determined period of time.

9. A method of monitoring physiological parameters of a ruminant animal, comprising:
generating a sensor signal from one or more sensors contained in a bolus orally administered to said ruminant animal, said sensor signal varies based on a corresponding change in one or more physiological parameters of said ruminant animal;

encoding said sensor signal from said one or more sensors as encoded physiological data corresponding to said one or more physiological parameters of said ruminant animal;

storing said encoded physiological data in a non-transitory computer readable media;

enabling a radio signal generator located within said bolus;

activating said radio signal generator to generate a radio signal to carry said encoded physiological data; and transmitting said radio signal with an antenna having a pair of electrically conductive loops disposed a distance apart and further comprising transmitting said radio signal through said antenna.

10. The method of claim 9, wherein said pair of electrically conductive loops each comprise a loop of conductive sheet material having an inner annular edge and an outer annular edge which join opposed loop faces.

11. The method of claim 10, wherein said antenna further comprises one or more vias interconnecting said pair of electrically conductive loops.

12. The method of claim 11, wherein said antenna further comprises a non-conductive sheet material disposed between said pair of electrically conductive loops.

13. A method of monitoring physiological parameters of a ruminant animal, comprising:
administering a bolus to said ruminant animal enabling or disabling one or more sensors in said bolus by execution of a computer code contained in a non-transitory computer readable media communicatively coupled to a processor;

generating a sensor signal from said one or more sensors which varies based on a corresponding change in one or more physiological parameters of said ruminant animal;

receiving a radio signal containing programming data; and re-programming said computer code contained within said non-transitory computer readable medium based on the radio signal containing programming data.

14. The method of claim 13, wherein said re-programming said computer code is based upon a pre-determined set of said physiological parameters to be sensed during a stage in a life cycle of said ruminant animal.

15. The method of claim 13, wherein said re-programming said computer code further comprises offsetting a difference in an amount of energy remaining in a power source and said an amount of energy required by said bolus to operate through a pre-determined period of time.

16. A method of monitoring physiological parameters of a ruminant animal, comprising:
generating a sensor signal from a first sensor located within a bolus disposed in the reticulorumen of said ruminant animal;
analyzing said sensor signal generated by said first sensor by execution of a power management module contained in a non-transitory computer readable medium communicatively coupled to a processor contained within said bolus;
comparing said sensor signal from said first sensor to a first pre-selected activation match threshold contained within a first pre-selected activation code; and
activating said bolus when the first pre-selected activation match threshold contained within the first pre-selected activation code is met.

17. The method of claim 16, further comprising:
generating a second sensor signal from a second sensor located within the bolus disposed in the reticulorumen of said ruminant animal;
comparing the second sensor signal from the second sensor to a second pre-selected activation code having a second pre-selected activation match threshold; and
activating said bolus when said first and second sensor signals from said first and second sensors meet said first pre-selected activation match threshold and said second pre-selected activation match threshold respectively.

18. The method of claim 16, further comprising orally administering said bolus to said ruminant animal.

19. The method of claim 18, further comprising:
generating a second sensor signal from a second sensor located within a bolus disposed in the reticulorumen of said ruminant animal;
comparing the second sensor signal from the second sensor to a second pre-selected activation code having a second pre-selected activation match threshold; and
activating said bolus when said first and second sensor signals from said first and second sensors meet said first pre-selected activation match threshold and said second pre-selected activation match threshold respectively.

* * * * *

UNITED STATES PATENT AND TRADEMARK OFFICE
CERTIFICATE OF CORRECTION

PATENT NO. : 10,231,644 B2
APPLICATION NO. : 14/738789
DATED : March 19, 2019
INVENTOR(S) : Nicholas P. Rettedal It is certified that error appears in the above-identified patent and that said Letters Patent is hereby corrected as shown below:

In the Claims

Column 22 Line 65 Claim 15 should read:
15. The method of claim 13, wherein said re-programming said computer code further comprises offsetting a difference in an amount of energy remaining in a power source and an amount of energy required by said bolus to operate through a pre-determined period of time.

Signed and Sealed this
Fourteenth Day of May, 2019

Andrei Iancu
*Director of the United States Patent and Trademark Office*

Disclaimer

10,231,644 B2 - Nicholas P. Rettedal, Loveland, CO (US); Stephen M. Weilnau and Scott R. Cockroft both of Greeley CO (US); Joseph Janus, IV, Loveland, CO (US). CALF BOLUS Patent dated August 16, 2016. Disclaimer filed October 24, 2024, 2024, by the assignee, ST Reproductive Technologies, LLC.

I hereby disclaim the following complete Claim 13 of said patent.

*(Official Gazette, December 10, 2024)*